(12) United States Patent
Bakircioglu et al.

(10) Patent No.: US 7,288,068 B2
(45) Date of Patent: Oct. 30, 2007

(54) AUTOMATIC OPTIMIZATION FOR ULTRASOUND MEDICAL IMAGING

(75) Inventors: Müge M. Bakircioglu, Sunnyvale, CA (US); Robert W. Steins, Santa Clara, CA (US); Constantine Simopoulos, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 317 days.

(21) Appl. No.: 10/737,204

(22) Filed: Dec. 15, 2003

(65) Prior Publication Data
US 2005/0131300 A1 Jun. 16, 2005

(51) Int. Cl.
A61B 8/06 (2006.01)

(52) U.S. Cl. .................................... 600/455
(58) Field of Classification Search ........ 600/440–441, 600/453–458; 128/916
See application file for complete search history.

(56) References Cited

U.S. PATENT DOCUMENTS

| | | | |
|---|---|---|---|
| 5,152,292 A | | 10/1992 | Karp |
| 5,363,849 A | * | 11/1994 | Suorsa et al. ............... 600/454 |
| 5,419,328 A | * | 5/1995 | Goh et al. .................. 600/443 |
| 5,487,389 A | | 1/1996 | Banjanin et al. |
| 5,494,037 A | | 2/1996 | Banjanin et al. |
| 5,544,659 A | | 8/1996 | Banjanin |
| 5,579,768 A | | 12/1996 | Klesenski |
| 5,634,465 A | | 6/1997 | Schmiesing et al. |
| 5,664,575 A | | 9/1997 | Banjanin et al. |
| 5,860,930 A | * | 1/1999 | Guracar ....................... 600/455 |
| 5,899,864 A | | 5/1999 | Arenson et al. |
| 5,923,278 A | * | 7/1999 | Poehler et al. ............ 342/25 C |
| 6,011,625 A | * | 1/2000 | Glass ........................ 356/496 |
| 6,142,931 A | | 11/2000 | Kaji |
| 6,162,176 A | | 12/2000 | Washburn et al. |
| 6,296,612 B1 | * | 10/2001 | Mo et al. .................... 600/455 |
| 6,309,357 B1 | | 10/2001 | Guracar et al. |
| 6,364,838 B1 | * | 4/2002 | Freiburger et al. .......... 600/455 |
| 6,398,733 B1 | | 6/2002 | Simopoulos et al. |
| 6,447,455 B2 | | 9/2002 | Bang et al. |

(Continued)

OTHER PUBLICATIONS

"Two-Dimensional Phase Unwrapping—Theory, Algorithms, and Software," by Dennis C. Ghiglia and Mark D. Pritt; a Wiley-Interscience publication; Copyright 1998 by John Wiley & Sons, Inc.; pp. 100-102- Chapter 4.

Primary Examiner—Francis J. Jaworski (57) ABSTRACT

Methods and systems are provided for automatic optimization for ultrasound medical imaging. In one approach, velocity values are unwrapped to avoid aliasing artifacts. Multi-dimensional phase unwrapping is applied to the velocity data. The unwrapped velocity information is used to optimize one or both of the velocity scale (e.g., pulse repetition frequency) and the imaging frequency. For optimizing the scale setting, the distribution of unwrapped velocities from a systolic time period of the heart cycle are used to identify the pulse repetition frequency. For optimizing the imaging frequency, a correlation as a function of depth shows the penetration depth for a given imaging frequency. In a dependent or independent approach, one or more thresholds for velocity or energy in flow imaging are adaptively selected as a function of an amount of clutter. Velocity or other energy information in addition to the clutter information may be used for selecting the thresholds. In yet another dependent or independent approach, displacement of an imaging plane or other change is detected and used to trigger an automatic update of an imaging parameter for a same or different mode.

40 Claims, 2 Drawing Sheets

U.S. PATENT DOCUMENTS

| | | |
|---|---|---|
| 6,478,742 B1 | 11/2002 | Kataoka |
| 6,579,238 B1 | 6/2003 | Simopoulos et al. |
| 6,679,844 B2 | 1/2004 | Loftman et al. |
| 6,689,064 B2* | 2/2004 | Hager et al. ................. 600/454 |
| 6,703,835 B2* | 3/2004 | Patch et al. ................. 324/307 |
| 6,733,454 B1 | 5/2004 | Bakircioğlu et al. |
| 6,891,370 B2* | 5/2005 | Cline et al. ................. 324/307 |
| 2002/0116414 A1 | 8/2002 | Mo et al. |
| 2003/0125624 A1* | 7/2003 | Shiki .......................... 600/443 |
| 2004/0122325 A1* | 6/2004 | Chambers et al. .......... 600/467 |

* cited by examiner

AUTOMATIC OPTIMIZATION FOR ULTRASOUND MEDICAL IMAGING

BACKGROUND

The present invention relates to automatic optimization for ultrasound medical imaging. One or more parameters are adaptively updated in a medical diagnostic ultrasound imaging system.

Different ultrasound parameters may be adaptively optimized. B-mode dynamic range and gain are adaptively optimized as a function of received ultrasound data. The adaptive optimization is performed at regular intervals, but irregular intervals based on a substantial change in an image may be provided as disclosed in U.S. Pat. No. 6,579,238, the disclosure of which is incorporated herein by reference. U.S. Pat. No. 6,733,454, the disclosure of which is incorporated herein by reference, discloses optimization of spectral Doppler parameters. For color flow imaging, other parameters may be updated. In U.S. Pat. No. 6,162,176, the distribution of the velocity values is used to identify a velocity threshold and color mapping. U.S. Pat. No. 6,478,742 discloses adjusting a pulse repetition frequency for automatic optimization. Maximum velocity along a single line of corrected velocity values is used to set the pulse repetition frequency. One dimensional reflection correction may result in residues or other artifacts in corrected velocities. The pulse repetition frequency may be set higher than optimal. For flow imaging parameters, the adaptive parameters may be incorrectly set or not fully optimized.

BRIEF SUMMARY

By way of introduction, the preferred embodiments described below include methods and systems for automatic optimization for ultrasound medical imaging. In one embodiment, velocity values are unwrapped to avoid aliasing artifacts. Multi-dimensional phase unwrapping is applied to the velocity data. The unwrapped velocity information is used to optimize one or both of the velocity scale (e.g., pulse repetition frequency) and the imaging frequency. For optimizing the scale setting, the distribution of unwrapped velocities from a systolic time period of the heart cycle are used to identify the pulse repetition frequency. For optimizing the imaging frequency, a correlation of velocity estimates as a function of depth shows the penetration depth for a given imaging frequency which gets lowered when the penetration depth is not sufficient. In a dependent or independent embodiment, one or more thresholds for velocity or energy in flow imaging are adaptively selected as a function of an amount of clutter. Velocity or energy information in addition to the clutter information may be used for selecting the thresholds. In yet another dependent or independent embodiment, displacement of an imaging plane or other change is detected and used to trigger an automatic update of an imaging parameter for a same or different mode.

In a first aspect, a method for automatic optimization in color Doppler velocity imaging is provided. Multi-dimensional phase unwrapping is applied to a set of velocity data representing a multi-dimensional region.

In a second aspect, a method for automatic optimization of thresholds for color Doppler imaging is provided. A clutter level is determined as a function of energy input to and energy output from a clutter filter. A threshold is selected as a function of the clutter level.

In a third aspect, a method for automatic optimization in color Doppler velocity imaging is provided. A correlation is determined as a function of depth between two sets of velocity data. An imaging frequency is altered as a function of the correlation.

In a fourth aspect, a method for automatic optimization of an ultrasound imaging parameter is provided. A displacement in an imaging region is detected. An imaging parameter selected from the group of: a flow imaging parameter, a velocity scale, a velocity threshold, an energy threshold, an imaging frequency, a beamforming parameter, a persistence value, spatial filter value and combinations thereof is automatically updated in response to the detection.

In a fifth aspect, a method for automatic optimization of an ultrasound imaging parameter is provided. A change is detected with data of a first ultrasound imaging mode. An imaging parameter of a second ultrasound imaging mode different than the first ultrasound imaging mode is automatically updated in response to the detection.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Ultrasound imaging parameters are optimized adaptively with no, minimal or other user input. For example, the imaging frequency, the velocity scale or thresholds for flow imaging are adaptively optimized as a function of ultrasound data. The description below deals with four different embodiments or aspects below: adaptively optimizing the velocity scale, imaging frequency, flow imaging thresholds, and triggering of automatic updates of an imaging parameter. These aspects or embodiments may be used independently or in any possible combination of two, three or all of the aspects.

Figure 1:
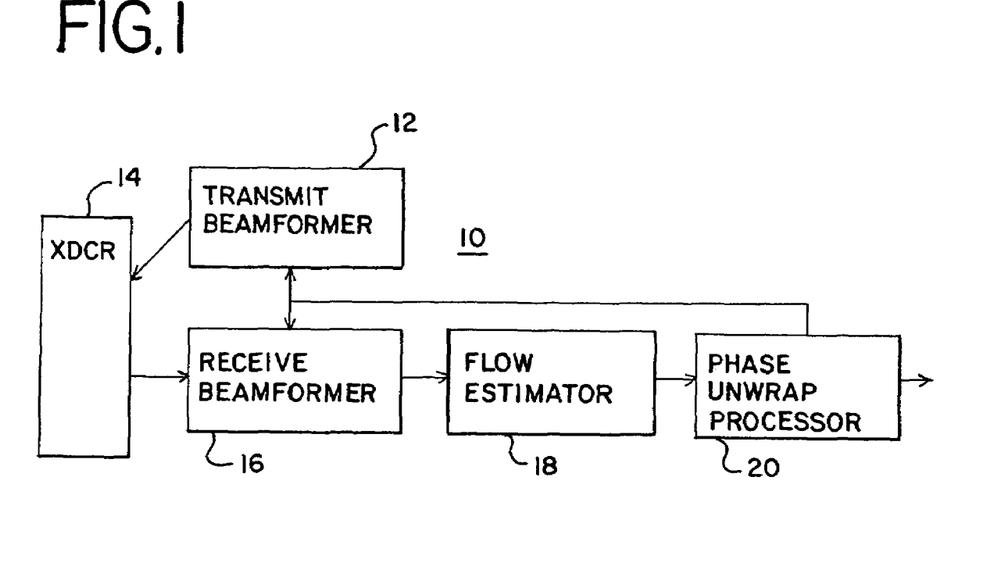
FIG. 1 is a block diagram of one embodiment of a system for automatic optimization of a velocity scale or imaging frequency.

FIG. 1 shows one embodiment of a system 10 for automatic optimization of the velocity scale or imaging frequency for flow imaging. The system 10 includes a transmit beamformer 12, a transducer 14, a receive beamformer 16, a flow estimator 18 and a phase unwrap processor 20. Additional, different or fewer components may be provided. For example, one or more of the components, such as the phase unwrap processor and/or the flow estimator 18, are separate and remote from the beamformers and transducers, such as in a work station. As another example, the phase unwrap processor 20 is integrated within the flow estimator 18 or not provided. Where the system 10 is a medical diagnostic ultrasound imaging system, further components connect with the phase unwrap processor or flow estimator 18, including a color mapping lookup table, a scan converter and a display.

The transmit beamformer 12 generates transmit waveforms for a plurality of channels. Due to relative timing and apodization of the waveforms across the transducer array 14, one or more transmit beams are generated. Plane wave generations may alternatively be used. The transmissions are separated by a pulse repetition interval, resulting in pulses being transmitted at a pulse repetition frequency. In response to each transmission, the receive beamformer 16 applies relative delays and apodizations to form samples representing one or more regions of a patient. Each sample is associated with a particular time based on the pulse repetition interval. The receive beamformer 16 generates radio frequency or in-phase and quadrature data for each sample.

The flow estimator 18 is a Doppler processor, general processor, digital signal processor, application specific integrated circuit, correlation processor, digital circuit, analog circuit, combinations thereof or other now known or later developed device for determining or estimating flow characteristics. The flow estimator 18 estimates velocities, energy, and/or variance from the sequence of signals representing a same location at different times. For a Doppler processor, the phase of the first lag of the autocorrelation function of the in-phase and quadrature components indicates the Doppler frequency shift, and the frequency shift information is converted to velocity information. The magnitude of the zeroth lag of the autocorrelation function provides energy. The scale or range of velocities determined by the flow estimator 18 is subject to the Nyquist sampling frequency, so the pulse repetition interval or pulse repetition frequency limits the velocity scale. Increasing the pulse repetition frequency allows for a larger scale. Where the velocity scale has a small range in comparison to the velocities of the flow being imaged, some velocity values may be aliased, resulting in incorrect estimation of velocity. A +/−2π wraparound phase error aliases some velocity data, such as high velocities.

The phase unwrap processor 20 is a general processor, a control processor, a digital signal processor, an application specific integrated circuit, a field programmable gate array, a digital circuit, an analog circuit, combinations thereof or other now know or later developed device. In one embodiment, the phase unwrap processor 20 is a single processor, but multi-processors may be provided. While shown as a separate device, the phase unwrap processor 20 may be implemented as a control or other processor within different components, such as a processor of the flow estimator 18, transmit beamformer 12, receive beamformer 16, a control processor for the system 10, or other now known or later developed processor within the system 10. In one embodiment, the phase unwrap processor 20 implements phase unwrapping processes, and a control processor of the transmit beamformer 12, receive beamformer 16 or both the transmit and receive beamformers 12, 16 determines the pulse repetition interval and imaging frequency from data output from the phase unwrap processor 20. A processor for implementing the phase unwrapping and setting of velocity scale and imaging frequency as used herein may include multiple different processors implementing the same function in parallel or different functions in series.

The phase unwrap processor 20 is operable to apply multi-dimensional phase unwrapping to a set of velocity data representing a multi-dimensional region and set one or both of the velocity scale and imaging of frequency as a function of the unwrapped velocities. A frame of data representing velocities within a two- or three-dimensional region is input to the phase unwrap processor 20. Using two- or three-dimensional phase unwrapping, a true phase or unaliased phase of the first lag of the autocorrelation function is calculated. The velocities or blood flow are treated as an analytic function, identifying residues separately and integrating the gradient of the phase along paths such that the integral of the gradient of the phase around the two-dimensional closed path is zero (i.e. path independence of the integral is assured). For setting the scale, a histogram of unaliased phase (e.g., velocity distribution) is used to identify a velocity scale that avoids some or all aliasing. The velocity scale is set at a minimum while avoiding undesirable aliasing. For example, a user selected velocity scale may be increased or decreased. For imaging frequency optimization, correlation associated with two different frames of unwrapped velocity or phase values is used to identify whether the imaging frequency should be lowered to avoid poor correlation at deeper depths.

In response to the different imaging frequency or velocity scale, the transmit beamformer 12 and the receive beamformer 16 are reconfigured to implement a different pulse repetition frequency and associated interval and different imaging frequency in either fundamental or harmonic receive modes. In addition, the new pulse repetition frequency is scaled by the ratio of the new imaging frequency to the old imaging frequency.

Figure 2:
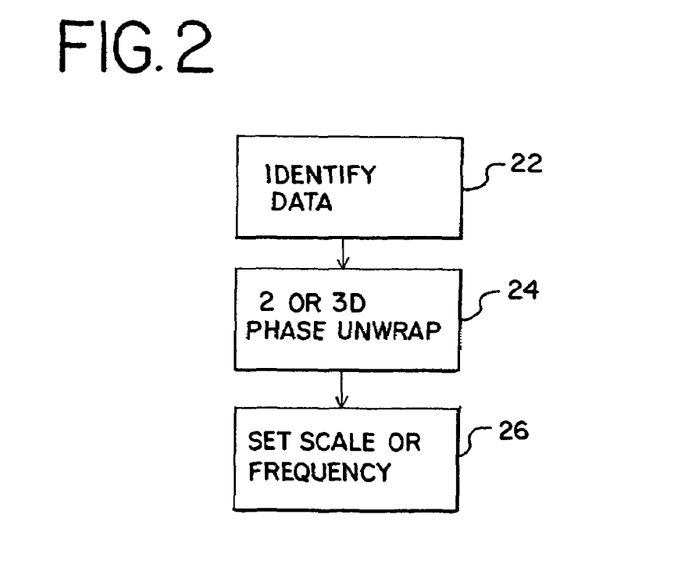
FIG. 2 is a flow chart diagram of a method for automatic optimization in velocity imaging of one embodiment.

FIG. 2 is a flow chart of one embodiment for automatic optimization in velocity imaging. The method of FIG. 2 is implemented using the system 10 of FIG. 1 or a different system. Different, additional or fewer acts may be provided.

In act 22, velocity data is identified for phase unwrapping. The velocity data provided is responsive to either a user set or a previously determined velocity scale. The velocity data represents one or more heart cycles. The data identified for unwrapping is one or more frames of data or a region of interest associated with a peak systole portion of the heart cycle. In alternative embodiments, different portions of the heart cycle are used. Velocities at peak systole are more likely associated with aliasing. In one embodiment, the frame of velocity data associated with peak systole is identified by summing the variance of velocity estimates for each of the frames or a region of interest of data or for each of a plurality of time periods. The sum is performed for each entire frame of data or for a same region or regions of each frame of data. The maximum sum identifies the systole. Other processes may be performed, such as identifying the peak systole using different parameters than variance, such as a sum of velocities, or using different functions, such as identifying the two or more frames of data having a highest average. In alternative embodiments, a heart monitor is used to identify the time periods or frames associated with peak systole. The identified velocity data may be spaced temporally away from the true peak.

In act 24, multi-dimensional phase unwrapping is applied to one or more sets of the velocity data representing one or more multi-dimensional regions. For example, two-dimensional phase unwrapping is performed to determine phase values of a set of velocity data representing a two-dimensional area. As another example, three-dimensional phase unwrapping is performed to determine the phase values of the set of velocity data representing a volume or three-dimensional region. The dimensions are spatial, but one dimension may be temporal.

Any now known or later developed multi-dimensional phase unwrapping algorithms may be used. In one embodiment, the measured or estimated phase is represented as:

$$\Phi=\arg(R(1)),\ \Phi\epsilon[0,\ 2\pi],$$

where the desired true phase is given by:

$$\psi=\Phi+2\pi k,$$

where R(1) is the first lag of an autocorrelation function or other phase or velocity estimate that may or may not be aliased and k is unknown integer value. To unwrap the phase or velocity values, the following equation is solved:

$$\psi(r)=\int_c \nabla\psi \cdot dr+\psi(r_0),$$

where c is a multi-dimensional path connecting the current range sample, r, to a range sample, $r_0$, of a known or assumed true phase. The value of $\psi(r)$ depends on the choice of the path c. If a current velocity or phase for a given range is not aliased, the unwrapped phase is the same. If the value is aliased, the phase value is different by $2\pi$ or other multiple, k, of $2\pi$. The multi-dimensional path is identified such that the integral of the phases around the closed path C is zero, as given by:

$$\int_c \nabla\psi \cdot dr=0$$

where $\nabla$ is a gradient and C the is closed path. This integral will not be equal to 0 if there are phase residues on the path. As part of multi-dimensional phase unwrapping, phase residues are selected along the path that have opposite values such that the integral more likely sums to zero. Any phase residues are selected to balance, such as matching a positive phase residue with a negative phase residue somewhere along the path. The path extends along two- or three-dimensions rather than just along a single line.

The unaliased phase is determined for each velocity value along the path and within the sets of frames of data. More than one path may be calculated for a given set of data for determining phase values for each of the velocities within the set. Alternatively, a single path is determined for a subset of all the velocities. For a given spatial location along the path, the gradient of the phase is integrated along the path from a known or assumed true phase value to the desired phase value. The integral of the gradient of the phase along the path provides the true phase at that spatial location provided the path contains a balanced number of residues. As a result, an aliased value is unaliased. Phase for a plurality of locations is determined. Any aliased phase is unwrapped or corrected to a true phase. This is equivalent to adding or subtracting $2\pi$ to the estimated phase in a 1D path if the difference from the previous estimate on the path is greater than $\pi$.

In act 26, one or both of the velocity scale and imaging frequency are set as a function of the results of the phase unwrapping in act 24. For setting the velocity scale as a function of the results, a histogram of the unwrapped velocities is formed. The histogram is populated by velocities unwrapped along one or more paths, such as velocities of the entire or only a portion of the set of velocity data. The pulse repetition interval or other velocity scale characteristic is calculated from the histogram distribution, such as the one corresponding to mean velocity plus two standard deviations. Alternatively, a velocity or phase associated with an inclusion of 95 or other percentage of the unwrapped velocities is selected. The pulse repetition interval is then calculated to provide a minimum velocity scale that does not alias the selected phase. Any other now known or later developed functions for selecting the velocity scale based on the results or the distribution of the histogram may be used.

In a further embodiment, the selected velocity scale is a function of both the results and a user aliasing selection. For example, the user selects an amount of aliasing by selecting a percentage of the distribution of the phases to be included within the velocity scale. For example, a slider is provided for selecting between 99% and 80%, between 99% and 95% or other range of inclusion or exclusion. As another example, the user selection is a selection of an offset from the mean velocity. The range of user selection or the function or thresholds used by the algorithm for selecting an amount of aliasing may be dependent on the type of examination, such as being different for imaging of the heart than for imaging of the aorta.

As an alternative or in addition to setting the velocity scale, the imaging frequency used for flow imaging is set in act 26. The imaging frequency is set as a function of the results of the phase unwrapping or as a function of other velocity values with or without unwrapping. Two different sets of data are identified, both associated with the peak systole period. For example, both sets of data are from a same heart cycle or from different cycles. None, one or all of the frames of the velocity data are a function of the results of phase unwrapping.

As yet other alternatives or additions to setting one or both of the velocity scale and imaging frequency used for flow imaging, one or combinations of multiple of baseline, parameters for auto-Doppler tracking, persistence, spatial filters, thresholds, and clutter filters are set in act 26. Parameters for auto-Doppler tracking may use unwrapped velocity information. For example, unwrapped velocities are used to set the scale of a base, initial or standard frame of velocity information in the embodiments disclosed in U.S. Pat. No. 6,733,454 rather than using a maximum velocity scale. Other spectral Doppler parameters may be set as a function of unwrapped velocities, such as setting a variable, function or other aspect of an algorithm for tracking a characteristic of spectral waveform (e.g., maximum velocity of the Doppler spectrum as a function of time). Persistence, spatial or other filtering may be varied as a function of the unwrapped velocities. For example, high unwrapped velocities indicate less spatial or temporal filtering. As discussed below, the thresholds for energy and/or velocity may be varied as a function of the unwrapped velocities. The clutter filter or characteristic of a clutter filter may also vary as a function of the unwrapped velocities. For example, a simple (e.g., three tap) clutter filter is used for high velocities, but a more complex clutter filter (e.g., four or more taps) with a tighter stop band is used for lower velocities.

A correlation between the sets of data as a function of depth is determined. The correlation as a function of depth provides a curve or a line. Any correlation function may be used, such as a cross correlation, a minimum sum of absolute differences, or other now known or later developed correlation or similarity functions. If the correlation between the two sets of data drops below a threshold as a function of depth, the imaging frequency is reduced. The reduction in correlation at greater depths indicates poor penetration. Lower frequencies are likely to increase the depth of penetration. The process is then repeated for the different imaging frequency to assure proper penetration depth given the user depth settings. Any of various functions may be used for determining an amount of decrease of the frequency, such as preprogrammed steps or adaptive as a function of the amount of correlation for deeper depths. The threshold for a correlation may be adjusted as a function of spatial resolution loss. As the frequencies decrease, the threshold may be decreased to minimize spatial resolution loss. The frequency may be increased where the correlation is above the threshold for the entire imaging depth. Using an iterative or process, the frequency is increased in an attempt to increase spatial resolution while maintaining the desired correlation as a function of the depth of penetration.

In one embodiment, the velocity scale or imaging frequency are set in response to an initial user configuration. Alternatively, the velocity parameters are set in response to user activation of a key or other selection. In yet other embodiments, the velocity parameters are set periodically or in response to a trigger.

Figure 3:
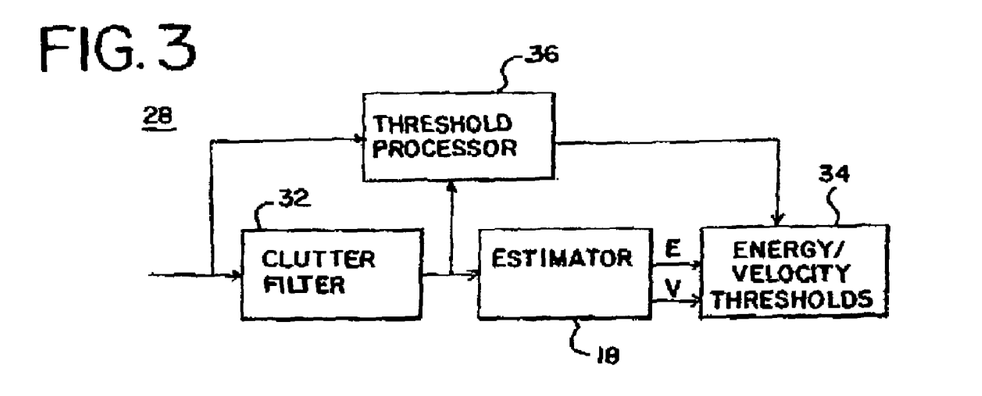
FIG. 3 is a block diagram of one embodiment of a processor for automatic optimization of thresholds for color Doppler imaging.
Figure 4:
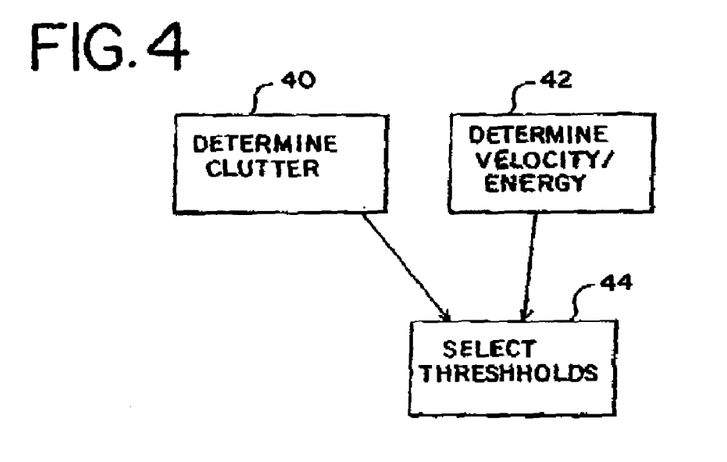
FIG. 4 is a flow chart diagram of a method for automatic optimization of thresholds in one embodiment.

Other flow imaging parameters may be set at a same or different times than the scale or imaging frequency, such as setting thresholds as a function of the results of the phase unwrapping and a clutter level. Flow imaging parameters include any of the various parameters discussed herein for color Doppler. Color Doppler imaging includes images based on velocity, energy, variance and combinations thereof. FIGS. 3 and 4 show a system and method, respectively, for determining thresholds and other filter settings in response to a clutter level with or without phase unwrapping for color Doppler imaging.

FIG. 3 shows a system 28 for automatic optimization of thresholds for velocity imaging. The system 28 includes a clutter filter 32, a flow estimator 18, an energy or velocity thresholder 34 and a threshold processor 36. Additional, different or fewer components may be provided. In one embodiment, the system 28 is incorporated within the system of FIG. 1, but may be incorporated in other or different systems.

The clutter filter 32 is a digital or analog filter for implementing a finite or infinite impulse response. Any now known or later developed clutter filter may be provided. In one embodiment, the clutter filter 32 includes a corner-turning memory for filtering the data along different firings of the same ultrasound line. The clutter filter 32 is operable to reduce or remove data associated with certain velocities, such as low velocities for moving tissue imaging. The output of the clutter filter 32 is provided to the threshold processor 36 and to the flow estimator 18. The flow estimator 18 operates as discussed above to estimate velocity, energy and/or variance from the clutter filtered data.

The energy or velocity thresholder 34 is a digital signal processing circuit, application specific integrated circuit, filter, general processor, look-up table, memory, filter, digital circuit, analog circuit, combinations thereof or any other now known or later developed thresholding device. The thresholder 34 acts to reduce or limit the maximum energy or velocities associated with such energies. The thresholder 34 is also operable to remove data associated with low velocities. The thresholder 34 may be implemented as part of the clutter filter 32, such as through selection of various filtering parameters to implement thresholding. The energy thresholding turns-off (removes or reduces) the color for velocities with an energy above a maximum energy, such as from bright stationary or slowly moving reflectors for which the clutter filter does not provide enough suppression.

The threshold processor 36 is a general processor, control processor, application specific integrated circuit, digital signal processor, digital circuit, analog circuit, combinations thereof or any other now known or later developed processor operable to determine a clutter level and select thresholds for application by the thresholder 30 and the thresholder 34. In response to the energy values input to the clutter filter 32 and output from the clutter filter 32, the threshold processor 36 is operable to determine a clutter level. One or more thresholds are then selected as a function of the clutter level. For example, the processor 36 includes a memory for a look-up table representing different N-dimensional surfaces for one or more thresholds as a function of one or more inputs including clutter.

FIG. 4 shows a flow chart of one embodiment of automatic optimization of thresholds for color Doppler imaging. The method of FIG. 4 is implemented using the system 28 of FIG. 3 or a different system.

In act 40, a clutter level is determined as a function of energy input into and energy output from a clutter filter. The clutter level is calculated as a difference in the energy input versus the energy output. For example, the energy input is divided by the energy output (i.e. ratio). As another example, the energy input is subtracted from the energy output. Other functions for determining clutter level may be used. In one embodiment, the clutter level is determined for each spatial location. The different clutter levels are then maintained separately or combined, such as combining for different regions or combining for an entire imaging region. For example, an average value is provided for an entire frame of data. As another example, two or more average values are provided for two distinct or overlapping regions of the same frame of data.

In act 42, energy and/or velocity values are determined for each of the plurality of spatial locations. For example, a flow estimator is used to identify velocity and energies. The velocity values may or may not be unwrapped. For each spatial location, a clutter value, a velocity value and an energy value is determined. In alternative embodiments, only the clutter or only a combination of two of the three above listed values is determined.

In act 44, a threshold is selected as a function of the clutter level. Any of various thresholds may be selected, such as a threshold for energy input to a clutter filter, a threshold for energy output from a clutter filter or estimator and a velocity threshold for data output from an estimator. Other thresholds for the same or different types of data and levels of processing may be used. In one embodiment, the threshold is selected as a function of clutter level, the energy output from an estimator and the velocity output from an estimator. In a further embodiment, each of the energy input threshold, the energy output threshold and the velocity threshold are selected as different functions of the clutter level, the energy output from an estimator and a velocity output from an estimator. Only one, only two, three or four or more different thresholds may be selected as a function of the clutter level and/or other values. The thresholds are selected for or from data of each spatial location, for or from data of multiple spatial location regions, or for or from data of an entire frame of data or associated imaging area. The input values are averaged or other function is used for determining an input value for selecting a threshold when a global threshold is to be chosen for imaging. For multi-spatial location regions, the threshold is selected as a function of an average, maximum, minimum or other determination of the inputs. For example, an average clutter level, a maximum energy and a minimum velocity associated with the region are used for selecting a threshold for that region. The same type of threshold with a different value is then selected for a different region that includes all different or overlapping spatial locations. Thresholds are smoothed across different regions to avoid abrupt changes. In yet another embodiment, the different thresholds are determined for different regions and then a compromise threshold is selected. For example, an average threshold value is selected. As another example, bimodal distribution of input values (e.g., high and low velocity flow in the same frame) is used to select a compromise threshold from the look-up table implementing any linear or non-linear function.

The energy thresholds are selected to remove flash, and the velocity thresholds are selected to remove information from slowly moving tissue in one embodiment. Input energy, output energy and velocity thresholds are selected as different functions of the clutter, velocity and energy in one embodiment. This input and output refers to the input and output of the clutter filter. The energy threshold is used to turn-off (select) velocity values based on the associated energies. Using a look-up table, three-dimensional surfaces implementing the different functions are provided for each of the thresholds with clutter, velocity and energy as inputs and an input energy, output energy and velocity threshold as outputs. Optimal thresholds are selected as a function of the input clutter, velocity and energy. For example, thresholds and clutter filters are provided for high energy, low clutter, and low velocity ranges for imaging venus flow, the portal vein or the hepatic vein. A different set of thresholds and associated clutter filtering are provided for the high velocity, high energy, low clutter ranges for carotid, cardiac and IVC imaging. For high clutter with low energy and low velocity ranges, settings are provided for testicular and thyroid imaging. For medium velocity, high clutter and low energy ranges, different settings are provided for kidney imaging. For high velocity with high energy and high clutter ranges, settings are provided for imaging the aorta. Yet further settings may be provided for high clutter with low energy and high velocity ranges for imaging of the hepatic artery or ovarian artery. Depending on the input clutter, energy and velocity values, the desired settings are selected. Additional, different or fewer settings, types of imaging, imaged object and groupings may be provided. In a further embodiment, more gradual settings of one or more of the thresholds are performed than the groupings discussed above. For example, a gradually varying surface is provided for each of the thresholds. While smoothly varying functions of the input values may be provided in some embodiments, step functions may be provided in other embodiments. The surfaces or threshold functions are implemented with a look-up table or through direct calculation. User experimentation or interpolation or extrapolation from various currently available filtering settings and associated thresholds may be used for identifying any one or all of the threshold functions. In general, the minimum velocity threshold is a decreasing function of velocity. The input and output energy thresholds are decreasing functions of clutter level but may be zero values or not used for high velocity signals regardless of clutter levels. Different functions may be provided for different transducer, types of examination, or pulse repetition frequencies.

During imaging, the current velocity, energy and/or clutter level are determined and used to select one or more thresholds or operating points of a desired filter. In one embodiment, the determination of the thresholds is an ongoing process that continually adapts to new sets of data. Alternatively, the thresholds are selected and only periodically updated or updated in response to a trigger.

For bimodal distributions, such as associated with two different regions of different flow or maximum velocities, a single threshold set is calculated for both regions or separate thresholds are used for each region. For using the same thresholds for both regions, the minimum velocity is biased towards the lower maximum velocity and the maximum energy thresholds for input and output energies are increased for flash suppression.

In one embodiment, different functions or other selections are performed in response to particular combinations of inputs. For example, the clutter level is identified as a high value with a velocity identified as a low value. A clutter filter is then selected as a complex notch filter, such as disclosed in U.S. Pat. No. 5,664,575, the disclosure of which is incorporated herein by reference. The complex notch filter is implemented through adaptive filtering where the signals are modulated to a mean velocity of the clutter through two-pass filtering. The minimum velocity threshold and the stopband bandwidth of the clutter filter are reduced for adaptive filtering. The stopband bandwidth and the number of taps of the clutter filter is then a function of the clutter energy.

To provide user control over the thresholds and any optimized clutter filter settings, a user filter key or other input may be provided for altering the adaptive selection of thresholds. For example, the user selects more or less filtering. Depending on the threshold, the value is changed in a particular direction. For example, in a high velocity and high energy case, the minimum velocity threshold is increased for more filtering and decreased for less filtering. As another example in a low energy and low velocity situation, an increase in the maximum input energy threshold provides more filtering, and a decrease provides less filtering. Adjustments of more than one threshold may be provided in other embodiments for more or less filtering in response to user input.

Figure 5:
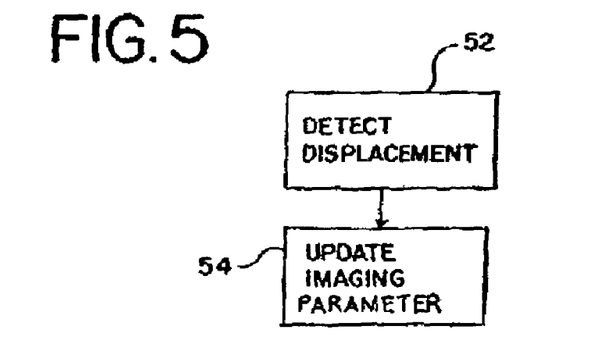
FIG. 5 is a flow chart diagram of one embodiment of a method for automatic optimization of an imaging parameter.

FIG. 5 shows one embodiment of a method for automatic optimization of an ultrasound imaging parameter. The method is implemented using the systems of FIG. 1, FIG. 3, a control processor of the same or different systems or processors in any now known or later developed ultrasound imaging system or sub-system. Optimal control settings for imaging in any of various modes vary between patients and different imaged parts of the anatomy. As discussed above, many different imaging parameters may be automatically set or determined. The automatic optimization may occur when requested by the user, such as through depressing a button or initially configuring a system for a particular exam. Alternatively, received data is continuously monitored and analyzed. When a change or other criteria are detected, a control processor or other processor causes a subsystem or algorithm responsible for optimizing an imaging parameter to perform the optimization. Any of various imaging parameters, such as adaptive persistence, spatial compounding, adaptive beamforming, pulse repetition intervals, velocity scale, flow mode thresholds, transmit power, display depth, imaging frequency or other now known or later developed imaging parameters are optimized in response to a detected change. This intermittent optimization avoids frame rate reduction due to optimization processes but applies the optimization for changes likely to effect whether a parameter continues to be optimum.

FIG. 5 represents one embodiment of monitoring continuously and requesting optimization when there is a change resulting from a displacement in the imaging plane. In act 52, displacement in the imaging region is detected. The imaging region may comprise a gate location, a line, an area, or a volume. For example, an elevation displacement in an imaging plane extending along azimuth and range dimensions is detected. The elevation dimension is orthogonal to the imaging plane or two dimensional imaging region.

Displacements within the imaging region (i.e., displacement in the azimuth and/or range dimensions) are detected in other embodiments.

The displacement is detected from any of various types of data, such as pre-detected, detected, B-mode or flow data. The data represents the entire imaging region or a sub-region of the entire imaging region. For example, the displacement is detected from B-mode data representing a sub-region of the imaging region. Only a central region, a low resolution version or sub-sampling of the imaging region, or other sub-region is monitored. As an alternative or in addition to sub-sampling, the data used for detecting displacement is acquired at a lower frame rate than imaging data, but a same frame rate or greater frame rate may be provided. For simultaneous imaging modes, such as the combination of B-mode and flow modes, the change is detected from the B-mode signal only, from both types of data or from color flow information only. The change is detected from data used for the current imaging parameter, such as detecting displacement from two- or three-dimensional flow data (e.g., color Doppler data) where flow imaging is provided. Alternatively, the displacement is detected using a different type of data or different mode than the current imaging mode, such as transmitting and receiving B-mode signals for detecting displacement while imaging without B-mode information.

The displacement is detected by calculating a similarity between different images of a sequence of images. The similarity or a value responsive to the similarity is then compared to a threshold to detect a particular displacement. Any of various functions may be used for determining the similarity, such as a maximum sum of absolute differences or other now known or later developed function indicating an amount of similarity.

For example, each image is divided into a plurality of regions. Each region includes one or more samples or pixels. The average intensities of B-mode data or average values of other data in each of the regions are calculated. The sum of the squares of the differences for each region from one image to another is determined. Alternatively, the sum of the squares of the differences is calculated for each entire image. As another example of a similarity, the rate of change of the sum of the squares of the differences indicates the similarity.

Each subsequent image is compared to the immediately preceding image, but may be compared to a first image or other image within the sequence. For example, a reference image is used determining the similarity from each of the other images within the sequence. The reference image may be a first image in the sequence, a combination of images from the sequence, or a previously acquired reference not part of the current sequence of images.

The average of the sum of the squares of the differences is compared to a threshold. The threshold is selected to indicate a displacement in the imaging region likely to result in unoptimal parameters, such as a displacement of an entire elevation beam width. Lesser or greater displacements may be detected.

In another embodiment for detecting displacement, a feature is identified. The feature within a first or reference image is then compared to the feature within a second image. For example, two or more images are segmented and quantities characterizing the morphology of the images are compared. The number of connected segments, the location of the segments, the size of the segments or other characterization is used for comparison. Segmentation is performed by automatic border detection or morphological image processing or other now known or later developed process for identifying a feature, such as applying a threshold to a gradient image. Unexpected changes in the morphology or feature indicate a displacement of an imaging plane. For example, the imaging plane intersects an organ having a particular area. Where the organ is relatively static in size and shape, changes in the shape or area of the organ indicate elevational displacement of the plane. For cyclically varying organs, the features are identified at a same portion of the cycle, or the differences in features as a function of the cycle are considered to not trigger optimization.

For flow imaging, such as Doppler imaging, color imaging or spectral Doppler imaging, B-mode data is used for determining the displacement. Alternatively, the flow imaging data is used. For example, changes in the pulsatility index (e.g., (maximum (systolic peak) velocity minus minimum velocity (end diastolic)) divided by the time averaged max velocity) or the resistivity index (e.g., (max–min)/max) over one or a number of estimated or actual heart cycles is used to indicate displacement. Where either of these indexes varies by a threshold amount over a portion or the entire cycle displacement is detected. Alternatively, changes in the peak velocity, mean velocity, energy or other flow imaging data are used to trigger the optimization.

For spectral Doppler optimization, the feature segmentation or morphological detection discussed above is used to distinguish a region of interest associated with a vessel or outside vessel. Alternatively, the system detects that the user has repositioned the spectral Doppler gate. This displacement of the spectral Doppler imaging region is detected for automatically optimizing or updating the optimization of spectral Doppler parameters. In one embodiment, the data is monitored continuously to detect displacement using a same algorithm or thresholds. Alternatively, the threshold varies as a function of previous detections. For example, a threshold difference increases for a time period immediately after a previous optimization.

Other hysteresis may be used. For example, the detection of displacement is delayed or stopped for a particular amount of time after an optimization is applied. In yet another embodiment, a displacement is detected. A delay is then provided before performing any optimization. If no further changes are detected within the time period, the optimization is performed. If further changes are detected, the time period begins again. Once the imaging region is stable, the optimization is performed, minimizing reductions in frame rates due to repeated undesired optimizations.

Other changes than displacement within an imaging region or of an imaging region may be detected for triggering optimization of an imaging parameter. For example, the presence of contrast agents newly flowing into an imaged region is detected where the imaging region maintains a same position. Contrast agent data or B-mode data intensities change due to the increase reflectivity provided by contrast agents. In response to the detected presence of contrast agents, one or more imaging parameters are automatically optimized.

In act 54, one or more imaging parameters are updated automatically in response to the detected displacement or other change. Imaging parameters include flow imaging parameters, such as a velocity scale, velocity threshold, energy threshold or imaging frequency discussed above or using different processes. For example, multi-dimensional or other phase unwrapping is applied to a set of velocity data representing a multi-dimensional region. The velocity scale or the imaging frequency is then set as a function of the phase unwrapped velocities. As another example, a clutter level is determined as a function of energy input to and energy output from a clutter filter. Energy or velocity thresholds are set as a function of the clutter level. Other flow imaging parameters, such as beamforming, persistence, spatial filtering, clutter filtering or combinations of multiple imaging parameters may be automatically updated. Beamformer parameters include delay profiles, apodization profiles, aberration correction or any other beamforming variable. Persistence values include any of various filtering weights or types of filters for performing persistence. Spatial filter values include weights or filters for spatial filtering (e.g. the size of a spatial filter) as well as variables within an algorithm for edge enhancement or edge detection. The same or different imaging parameters are provided for automatic optimization in B-modes operation. U.S. Pat. No. 6,733,454, the disclosure of which is incorporated herein by reference, discloses automatic optimization of some example parameters for spectral Doppler imaging. Other now known or later developed imaging parameters for any of various now known or later developed imaging modes may be automatically updated in response to a detected change or displacement.

The automatic optimization is provided by adaptively updating one or more parameters. The parameter value is selected as a function of received data. As a result, the imaging parameter adapts to the current imaging plane or flow state.

In another embodiment of the method for automatic optimization of an ultrasound imaging parameter, different ultrasound imaging modes are used in combination. A change is detected with data of a first ultrasound imaging mode. For example, a displacement in an imaging plane is detected from one of B-mode or flow mode data. Alternatively, the change is detected from contrast agent imaging mode data, harmonic imaging mode data or Doppler mode data. Other now known or later developed modes of imaging may be used, such as imaging modes using multiple transmissions with different phasing or apodization and combinations of responsive receive signals for isolating frequencies of a desired content.

In response to the detected change, an imaging parameter of a second imaging mode different than the first imaging mode is automatically updated. For example where B-mode data is used to detect the change, the imaging parameter for a flow mode imaging is automatically updated. Conversely, where flow mode data is used for detecting the change, an imaging parameter for B-mode imaging is automatically updated. Other modes may be used in combination, such as either flow mode or B-mode in combination with a third type of mode. Any now known or later developed modes may be used for detecting the change or for automatic updating of an associated imaging parameter. For example, any of the imaging parameters discussed above for flow imaging, B-mode imaging or any other mode of imaging are automatically updated in response to the detected change.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and the scope of this invention.

We claim:

1. In a method for automatic optimization in color Doppler velocity imaging, an improvement comprising:

(a) applying multidimensional phase unwrapping to a set of velocity data representing a multidimensional region;
(b) setting a velocity scale, baseline, a parameter for auto-Doppler tracking, a persistence parameter, a spatial filter parameter, a threshold, a clutter filter parameter, an imaging frequency, or combinations thereof as a function of results of (a); and
(c) imaging as a function of the setting.

2. The method of claim 1 wherein (b) comprises:
(b1) determining a histogram of unwrapped velocities of the set of velocity data; and
(b2) selecting the velocity scale as a function of distribution of the histogram.

3. The method of claim 1 wherein (a) comprises determining a two dimensional phase unwrapping to each value of the set of velocity data, the multidimensional region being an area.

4. The method of claim 1 wherein (a) comprises determining a three dimensional phase unwrapping to each value of the set of velocity data, the multidimensional region being a volume.

5. The method of claim 1 further comprising:
(d) setting thresholds as a function of the results of (a) and a measure of clutter.

6. The method of claim 1 further comprising:
(d) identifying the set of velocity data prior to (a) as associated with a systole period of a heart cycle.

7. The method of claim 1 wherein (b) comprises setting the imaging frequency as a function of the results of (a), the imaging frequency being for flow imaging.

8. The method of claim 7 wherein (b) comprises:
(b1) determining a correlation as a function of depth between two frames of velocity data, one of the frames of velocity data being a function of the results of (a); and
(b2) reducing the imaging frequency in response to a decrease in the correlation at greater depths.

9. A system for automatic optimization in velocity imaging, the system having at least one processor operable to implement acts (a) and (b) of claim 1.

10. The method of claim 1 further comprising:
(d) detecting a displacement in an imaging region; and
(e) triggering (a) and (b) in response to (d).

11. In a method for automatic optimization in color Doppler velocity imaging, an improvement comprising:
(a) applying multidimensional phase unwrapping to a set of velocity data representing a multidimensional region wherein (a) comprises:
(a1) determining a multidimensional closed path with the gradient of the phase integrating to zero;
(a2) determining a phase for a plurality of locations along the multidimensional path; and
(b) adapting imaging as a function of the phase.

12. The method of claim 11 wherein (a1) comprises selecting phase residues along the multidimensional pat of opposite values.

13. In a method for automatic optimization in color Doppler velocity imaging, an improvement comprising:
(a) applying multidimensional phase unwrapping to a set of velocity data representing a multidimensional region;
(b) setting the velocity scale as a function of the results of (a);
(c) performing (b) as a function of the results and a user aliasing selection; and
(d) imaging as a function of the setting.

14. A method for automatic optimization of a threshold for color Doppler imaging, the method comprising:
- (a) determining a clutter level as a function of energy input to and energy output from a clutter filter;
- (b) selecting a threshold as a function of the clutter level; and
- (c) imaging as a function of the threshold.

15. The method of claim 14 wherein (a) comprises dividing or subtracting the energy input by the energy output.

16. The method of claim 14 wherein (b) comprises selecting an energy input threshold, an energy output threshold, a velocity threshold, or combinations thereof.

17. The method of claim 16 wherein (b) comprises selecting each of the energy input threshold, the energy output threshold and the velocity threshold as a function of the clutter level, energy output and velocity.

18. The method of claim 16 wherein (b) comprises selecting at least two of the thresholds from the group of: the energy input threshold, the energy output threshold and the velocity threshold as a function of the clutter level.

19. The method of claim 16 wherein (b) comprises selecting the energy input or energy output thresholds.

20. The method of claim 16 further comprising:
- (d) identifying the clutter level as high and a velocity as low; and
- (e) selecting a clutter filter as a complex notch filter as a function of the identification of (d).

21. The method of claim 14 wherein (b) comprises selecting the threshold as a function of the clutter level, energy output and velocity.

22. The method of claim 21 further comprising:
- (d) applying multidimensional phase unwrapping to a set of velocity data representing a multidimensional region;
- wherein (b) comprises selecting as a function of the velocity, the velocity being from results of (d).

23. The method of claim 14 wherein (b) comprises selecting the threshold for a first region and an additional threshold of a same type for a second region different than the first region.

24. The method of claim 14 further comprising:
- (d) applying multidimensional phase unwrapping to a set of velocity data representing a multidimensional region; and
- (e) setting an imaging frequency as a function of results of (a).

25. A system for automatic optimization of thresholds for velocity imaging, the system comprising a processor operable to perform the acts (a) and (b) of claim 14.

26. The method of claim 14 further comprising:
- (d) detecting a displacement in an imaging region; and
- (e) triggering (a) and (b) in response to (d).

27. A method for automatic optimization in velocity imaging, the method comprising:
- (a) determining a correlation as a function of depth between two sets of velocity data;
- (b) altering an imaging frequency as a function of the correlation; and
- (c) imaging as a function of the altered imaging frequency.

28. The method of claim 26 further comprising:
- (d) identifying the two sets of velocity data as frames of data associated with a peak systole period.

29. The method of claim 27 wherein (b) comprises decreasing the imaging frequency where the correlation decreases for greater depths.

30. The method of claim 27 further comprising:
- (d) detecting a displacement in an imaging region; and
- (e) triggering (a) and (b) in response to (d).

31. A method for automatic optimization of an ultrasound imaging parameter, the method comprising:
- (a) detecting a displacement associated with an imaging region;
- (b) automatically updating an imaging parameter selected from the group of: a flow imaging parameter, a velocity scale, a velocity threshold, an energy threshold, an imaging frequency, a beamforming parameter, a persistence value, spatial filter value and combinations thereof in response to (a); and
- (c) imaging as a function of the updated imaging parameter.

32. The method of claim 31 wherein (b) comprises:
- (b1) applying multidimensional phase unwrapping to a set of velocity data representing a multidimensional region; and
- (b2) setting the velocity scale, or the imaging frequency as a function of results of (b1).

33. The method of claim 31 wherein (b) comprises:
- (b1) determining a clutter level as a function of energy input to and energy output from a clutter filter; and
- (b2) selecting the energy threshold, or the velocity threshold as a function of the clutter level.

34. The method of claim 31 wherein (a) comprises detecting elevation, azimuth, range displacement, or combinations thereof in an azimuth and range imaging plane and wherein (b) comprises adaptively updating the imaging parameter.

35. The method of claim 31 wherein (a) comprises detecting the displacement from B-mode data representing a sub-region of the imaging region.

36. The method of claim 35 wherein (b) comprises automatically updating the flow imaging parameter.

37. The method of claim 31 wherein (a) comprises:
- (a1) calculating a similarity; and
- (a2) comparing the similarity or a value responsive to the similarity to a threshold.

38. The method of claim 31 wherein (a) comprises:
- (a1) identifying a feature; and
- (a2) comparing the feature within a first image to the feature within a second image.

39. The method of claim 31 wherein (a) comprises detecting a repositioning of a spectral Doppler gate.

40. The method of claim 31 wherein (a) comprises detecting the displacement of an imaging plane from flow data.

* * * * *